United States Patent
Hoey et al.

(10) Patent No.: US 8,272,383 B2
(45) Date of Patent: Sep. 25, 2012

(54) SYSTEMS AND METHODS FOR MALE STERILIZATION

(75) Inventors: Michael Hoey, Shoreview, MN (US); John H. Shadduck, Tiburon, CA (US)

(73) Assignee: NxThera, Inc., St. Paul, MN (US)

( * ) Notice: Subject to any disclaimer, the term of this patent is extended or adjusted under 35 U.S.C. 154(b) by 334 days.

(21) Appl. No.: 12/436,703

(22) Filed: May 6, 2009

(65) Prior Publication Data

US 2009/0277457 A1 Nov. 12, 2009

Related U.S. Application Data

(60) Provisional application No. 61/126,620, filed on May 6, 2008.

(51) Int. Cl.
*A61F 6/02* (2006.01)
*A61B 18/18* (2006.01)
*A61B 18/04* (2006.01)

(52) U.S. Cl. .............................. 128/842; 606/24; 606/27

(58) Field of Classification Search .......... 128/842–843, 128/830, 831, 832, 833; 606/24, 41, 27, 606/135, 194, 13, 21; 604/515, 544, 113, 604/291, 96.01, 93.01, 48; 623/23.7; 424/430; 607/116, 143, 101, 105; 600/411
See application file for complete search history.

(56) References Cited

U.S. PATENT DOCUMENTS

| | | | |
|---|---|---|---|
| 4,672,963 A | 6/1987 | Barken | |
| 4,950,267 A | 8/1990 | Ishihara et al. | |
| 5,312,399 A | 5/1994 | Hakky et al. | |
| 5,330,518 A | 7/1994 | Neilson et al. | |
| 5,366,490 A | 11/1994 | Edwards et al. | |
| 5,370,609 A | 12/1994 | Drasler et al. | |
| 5,370,675 A | 12/1994 | Edwards et al. | |
| 5,385,544 A | 1/1995 | Edwards et al. | |
| 5,409,453 A | 4/1995 | Lundquist et al. | |
| 5,421,819 A | 6/1995 | Edwards et al. | |
| 5,435,805 A | 7/1995 | Edwards et al. | |
| 5,470,308 A | 11/1995 | Edwards et al. | |
| 5,470,309 A | 11/1995 | Edwards et al. | |
| 5,484,400 A | 1/1996 | Edwards et al. | |

(Continued)

FOREIGN PATENT DOCUMENTS

WO WO 92/10142 A1 6/1992

(Continued)

OTHER PUBLICATIONS

Hoey et al.; U.S. Appl. No. 12/614,218 entitled "Systems and Methods for Treatment of Prostatic Tissue," filed Nov. 6, 2009.

(Continued)

*Primary Examiner* — Patricia Bianco
*Assistant Examiner* — Ophelia Hawthorne
(74) *Attorney, Agent, or Firm* — Shay Glenn LLP (57) ABSTRACT

An energy delivery probe is provided that may include any of a number of features. One feature of the energy delivery probe is that it can apply energy to tissue, such as a duct, to shrink, damage, or occlude the duct. In some embodiments, the energy can be applied with a vapor media. In some embodiments, the duct can be a ductus deferens or an ejaculatory duct of the male reproductive system. Another feature of the energy delivery probe is that it can utilize an inflatable member to form a seal to contain the vapor media. Methods associated with use of the energy delivery probe are also covered.

27 Claims, 5 Drawing Sheets

U.S. PATENT DOCUMENTS

| | | | |
|---|---|---|---|
| 5,531,676 A | 7/1996 | Edwards et al. | |
| 5,542,915 A | 8/1996 | Edwards et al. | |
| 5,542,916 A | 8/1996 | Hirsch et al. | |
| 5,545,171 A | 8/1996 | Sharkey et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,673 A | 9/1996 | Edwards et al. | |
| 5,588,960 A | 12/1996 | Edwards et al. | |
| 5,591,125 A | 1/1997 | Edwards et al. | |
| 5,599,294 A | 2/1997 | Edwards et al. | |
| 5,601,591 A | 2/1997 | Edwards et al. | |
| 5,630,794 A | 5/1997 | Lax et al. | |
| 5,667,488 A | 9/1997 | Lundquist et al. | |
| 5,672,153 A | 9/1997 | Lax et al. | |
| 5,720,718 A | 2/1998 | Rosen et al. | |
| 5,720,719 A | 2/1998 | Edwards et al. | |
| 5,797,903 A | 8/1998 | Swanson et al. | |
| 5,830,179 A | 11/1998 | Mikus et al. | |
| 5,849,011 A | 12/1998 | Jones et al. | |
| 5,871,481 A | 2/1999 | Kannenberg et al. | |
| 5,873,877 A | 2/1999 | McGaffigan et al. | |
| 5,944,715 A | 8/1999 | Goble et al. | |
| 5,957,922 A | 9/1999 | Imran | |
| 5,964,752 A | 10/1999 | Stone | |
| 5,964,756 A | 10/1999 | McGaffigan et al. | |
| 5,976,123 A | 11/1999 | Baumgardner et al. | |
| 6,017,361 A | 1/2000 | Mikus et al. | |
| 6,036,713 A | 3/2000 | Kieturakis | |
| 6,077,257 A | 6/2000 | Edwards et al. | |
| 6,113,593 A | 9/2000 | Tu et al. | |
| 6,206,847 B1 | 3/2001 | Edwards et al. | |
| 6,238,391 B1 | 5/2001 | Olsen et al. | |
| 6,241,702 B1 | 6/2001 | Lundquist et al. | |
| 6,258,087 B1 | 7/2001 | Edwards et al. | |
| 6,423,027 B1 | 7/2002 | Gonon | |
| 6,440,127 B2 | 8/2002 | McGovern et al. | |
| 6,551,300 B1 | 4/2003 | McGaffigan | |
| 6,607,529 B1* | 8/2003 | Jones et al. | 606/47 |
| 6,669,694 B2 | 12/2003 | Shadduck | |
| 6,716,252 B2 | 4/2004 | Lazarovitz et al. | |
| 6,719,738 B2 | 4/2004 | Mehier | |
| 6,726,696 B1 | 4/2004 | Houser et al. | |
| 6,730,079 B2 | 5/2004 | Lovewell | |
| 6,760,616 B2 | 7/2004 | Hoey et al. | |
| 6,780,178 B2 | 8/2004 | Palanker et al. | |
| 6,827,718 B2 | 12/2004 | Hutchins et al. | |
| 6,905,475 B2 | 6/2005 | Hauschild et al. | |
| 6,969,376 B2 | 11/2005 | Takagi et al. | |
| 7,014,652 B2 | 3/2006 | Cioanta et al. | |
| 7,089,064 B2 | 8/2006 | Manker et al. | |
| 7,130,697 B2 | 10/2006 | Chornenky et al. | |
| 7,261,709 B2 | 8/2007 | Swoyer et al. | |
| 7,261,710 B2 | 8/2007 | Elmouelhi et al. | |
| 7,335,197 B2 | 2/2008 | Sage et al. | |
| 7,429,262 B2 | 9/2008 | Woloszko et al. | |
| 7,470,228 B2* | 12/2008 | Connors et al. | 600/30 |
| 7,674,259 B2* | 3/2010 | Shadduck | 606/41 |
| 2002/0177846 A1* | 11/2002 | Mulier et al. | 606/27 |
| 2003/0069575 A1 | 4/2003 | Chin et al. | |
| 2004/0068306 A1 | 4/2004 | Shadduck | |
| 2004/0230316 A1 | 11/2004 | Cioanta et al. | |
| 2006/0135955 A1 | 6/2006 | Shadduck | |
| 2006/0178670 A1 | 8/2006 | Woloszko et al. | |
| 2006/0224154 A1 | 10/2006 | Shadduck et al. | |
| 2006/0276871 A1 | 12/2006 | Lamson et al. | |
| 2007/0032785 A1 | 2/2007 | Diederich et al. | |
| 2007/0142846 A1 | 6/2007 | Catanese, III et al. | |
| 2008/0021484 A1 | 1/2008 | Catanese, III et al. | |
| 2008/0021485 A1 | 1/2008 | Catanese, III et al. | |
| 2008/0033232 A1 | 2/2008 | Catanese, III et al. | |
| 2008/0033458 A1 | 2/2008 | McLean et al. | |
| 2008/0033488 A1 | 2/2008 | Catanese, III et al. | |
| 2008/0039833 A1 | 2/2008 | Catanese, III et al. | |
| 2008/0039872 A1 | 2/2008 | Catanese, III et al. | |
| 2008/0039874 A1 | 2/2008 | Catanese, III et al. | |
| 2008/0039875 A1 | 2/2008 | Catanese, III et al. | |
| 2008/0039876 A1 | 2/2008 | Catanese, III et al. | |
| 2008/0039893 A1 | 2/2008 | McLean et al. | |
| 2008/0039894 A1 | 2/2008 | Catanese, III et al. | |
| 2008/0046045 A1 | 2/2008 | Yon et al. | |
| 2008/0132826 A1 | 6/2008 | Shadduck et al. | |
| 2008/0208187 A1 | 8/2008 | Bhushan et al. | |
| 2008/0249399 A1 | 10/2008 | Appling et al. | |
| 2008/0275440 A1 | 11/2008 | Kratoska et al. | |
| 2009/0018553 A1 | 1/2009 | McLean et al. | |
| 2009/0054871 A1* | 2/2009 | Sharkey et al. | 604/515 |
| 2009/0149846 A1 | 6/2009 | Hoey et al. | |
| 2009/0216220 A1 | 8/2009 | Hoey et al. | |
| 2009/0227998 A1 | 9/2009 | Aljuri et al. | |
| 2010/0016757 A1 | 1/2010 | Greenburg et al. | |
| 2010/0049031 A1 | 2/2010 | Fruland et al. | |
| 2010/0286679 A1 | 11/2010 | Hoey et al. | |
| 2010/0292767 A1 | 11/2010 | Hoey et al. | |
| 2010/0298948 A1 | 11/2010 | Hoey et al. | |

FOREIGN PATENT DOCUMENTS

| | | | |
|---|---|---|---|
| WO | WO 01/24715 A1 | 4/2001 | |
| WO | WO 2006/004482 A1 | 1/2006 | |

OTHER PUBLICATIONS

Shadduck et al.; U.S. Appl. No. 12/614,238 entitled "Systems and Methods for Treatment of Prostatic Tissue," filed Nov. 6, 2009.

Hoey et al.; U.S. Appl. No. 12/614,226 entitled "Systems and Methods for Treatment of BPH," filed Nov. 6, 2009.

Shadduck et al.; U.S. Appl. No. 12/687,722 entitled "Systems and Methods for Treatment of Prostatic Tissue," filed Jan. 14, 2010.

Hoey et al.; U.S. Appl. No. 12/687,734 entitled "Medical Systems and Methods," filed Jan. 14, 2010.

Hoey et al.; U.S. Appl. No. 13/072,573 entitled "Systems and Methods for Prostate Treatment," filed Mar. 25, 2011.

Hoey et al.; U.S. Appl. No. 13/352,198 entitled "Systems and methods for prostate treatment," filed Jan. 17, 2012.

Hai; Photoselective Vaporization Prostatectomy: A Palliative Treatment Option for Men with Urinary Obstruction Secondary to Prostate Cancer; PCRI Prost.Cancer Rsrch.lnst. Reprint.from PCRI Insights Nov. 2005, vol. 8(4); Dwnld from http://www.prostate-cancer.org/pcricms/node/233 on May 10, 2012; 4 pages.

* cited by examiner

SYSTEMS AND METHODS FOR MALE STERILIZATION

CROSS REFERENCE TO RELATED APPLICATIONS

This application claims the benefit under 35 U.S.C. 119 of U.S. Provisional Patent Application No. 61/126,620, filed May 6, 2008, titled "MEDICAL SYSTEM AND METHOD OF USE." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to methods for male contraception and devices used for the delivery of ablative energy to occlude a patient's ejaculatory ducts or vas differentia.

BACKGROUND OF THE INVENTION

Several methods are known in the field of male contraception, with surgical vasectomies and occlusion of the vas deferens with implants being the most common approaches.

A surgical vasectomy can be an effective method for causing male sterility, however, the procedure itself can be painful as it requires incisions to access the vas deferens, and in many cases pain can linger over the long term.

Another method of male contraception utilizes plugs that are surgically implanted in the vas deferens. The plugs block the path of sperm from the testicles to the ejaculatory ducts and urethra. Such surgical methods of implanting plugs can be expensive and time-consuming.

Accordingly, the present invention is directed to provide safe, efficient, and timely methods for male sterilization procedures. Additionally, the present invention is directed to providing apparatus that can be easily positioned within the prostate during male sterilization procedures.

SUMMARY OF THE INVENTION

Generally, the present invention contemplates the use of a vapor delivery probe to occlude a duct in the male reproductive system.

One aspect of the invention includes a method of male sterilization, comprising introducing a vapor delivery tool into or proximate to a duct of a male reproductive system, and delivering vapor media through the vapor delivery tool into the duct to occlude the duct.

In some embodiments of the method, the introducing step comprises introducing the vapor delivery tool transurethrally. In other embodiments, the introducing step comprises introducing the vapor delivery tool through a skin incision.

In further embodiments, the method further comprises forming a seal in a urethra to contain the vapor media Forming the seal can further direct the vapor media into the duct. In some embodiments, the step of forming the seal includes expanding an expandable member. In other embodiments, forming the seal includes expanding an expandable portion of the vapor delivery tool.

In some embodiments, the vapor media damages a wall of the duct. In other embodiments, the vapor media denatures collagen in the wall of the duct.

In some embodiments, the vapor media has a temperature of at least 60° C. In other embodiments, the vapor media has a temperature between approximately 60° C. and 100° C.

In some embodiments, the vapor media is delivered for an interval ranging from approximately 0.1 second to 30 seconds.

In additional embodiments, the vapor media carries a second composition. The second composition can comprise a pharmacologic agent or a sealant, for example.

In some embodiments of the invention, the duct is an ejaculatory duct. In other embodiments, the duct is a ductus deferens.

In some embodiments, male sterilization method is provided that comprises introducing an energy delivery tool into or proximate to a duct of a male reproductive system, and applying energy by a fluid from the delivery tool to occlude the duct.

In some embodiments, the fluid is selected from the group consisting of a cryogenic fluid, a heated liquid, and high temperature vapor.

A system for male sterilization is also provided, comprising, a vapor delivery probe configured for transurethral introduction into or proximate to a duct of a male reproductive system, and a vapor source in fluid communication with the vapor delivery probe, the vapor source adapted to deliver a vapor media through the vapor delivery probe into the duct to modify the duct.

In some embodiments, the condensable vapor has a temperature of approximately 60° to 100° C.

In other embodiments, the system further comprises a source for introducing a second composition through the vapor delivery probe.

In additional embodiments, the system further comprises a controller configured to control a vapor delivery interval.

In other embodiments, the system further comprises at least one expandable member configured to contain the vapor media. The at least one expandable member can be an inflatable balloon, for example.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

In the drawings.

DETAILED DESCRIPTION OF THE INVENTION

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

Figure 1:
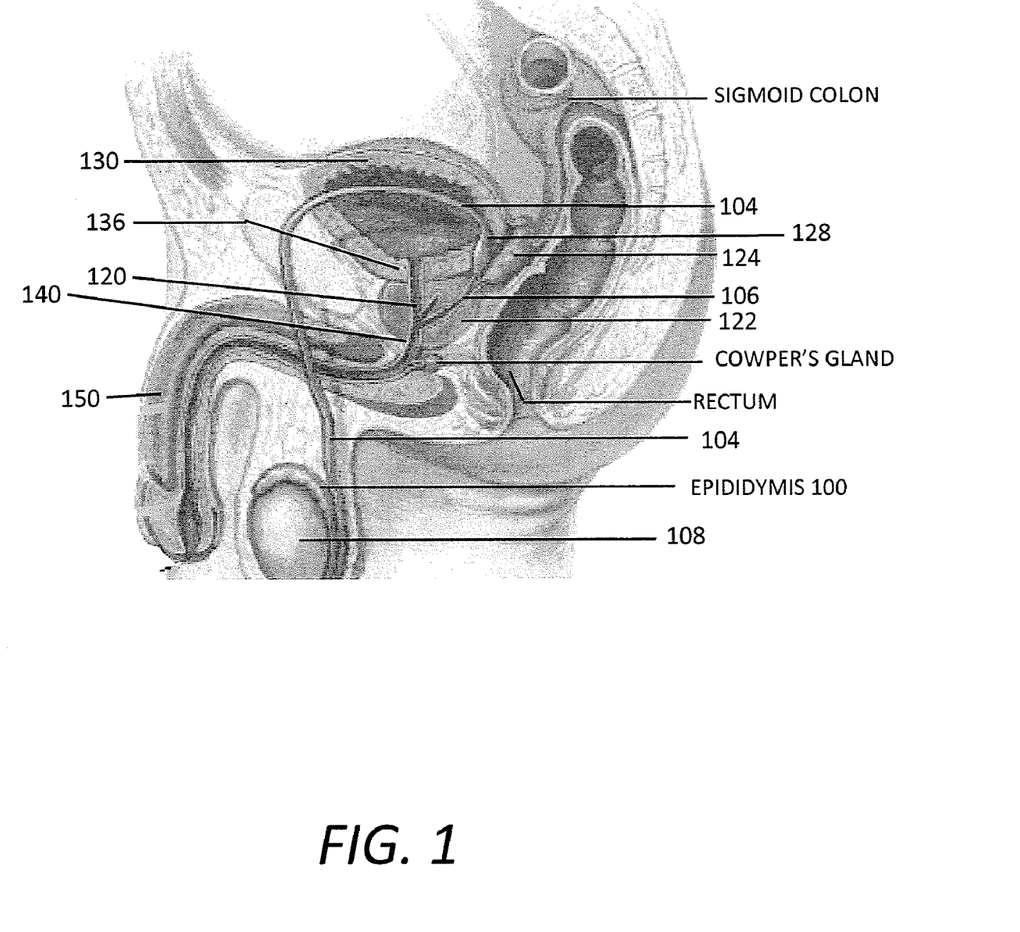
FIG. 1 is a sectional schematic view the male reproductive tract and urogenital anatomy.

FIG. 1 illustrates an anatomical view of the male reproductive system. As shown in FIG. 1, the epididymis 100, vas deferens 104 (or ductus deferens) and ejaculatory ducts 106 form the sperm canal. Together they extend from the testes 108 to the prostatic urethra 120. The vas deferens 104 is the continuation of the duct of the epididymis 100, which ascends along the back border of the testes through the pelvis toward the base of the prostate 122, where it is joined by the seminal vesicle 124 to form the ejaculatory ducts 106. The vas deferens has walls of smooth muscle that provide peristaltic contractions to move sperm toward the ampulla 128—a portion of the vas deferens that is dilated near the base of the urinary bladder 130.

The prostate gland 122 is the largest accessory gland in the male reproductive system. Together with the testes and seminal vesicles 124, the prostate's primary function is the production of semen. The prostate is a walnut-sized organ that surrounds the prostatic urethra 120 that adds secretions to sperm during the ejaculation of semen. Superiorly, the base of the prostate 122 is contiguous with the bladder neck 136 and inferiorly its apex 140 adjoins the urogenital diaphragm. The prostate 120 can be rounded at the top and can narrow to form a blunt point at apex 140. The prostate diameter in the broadest area can be about 4 cm.

Figure 2A:
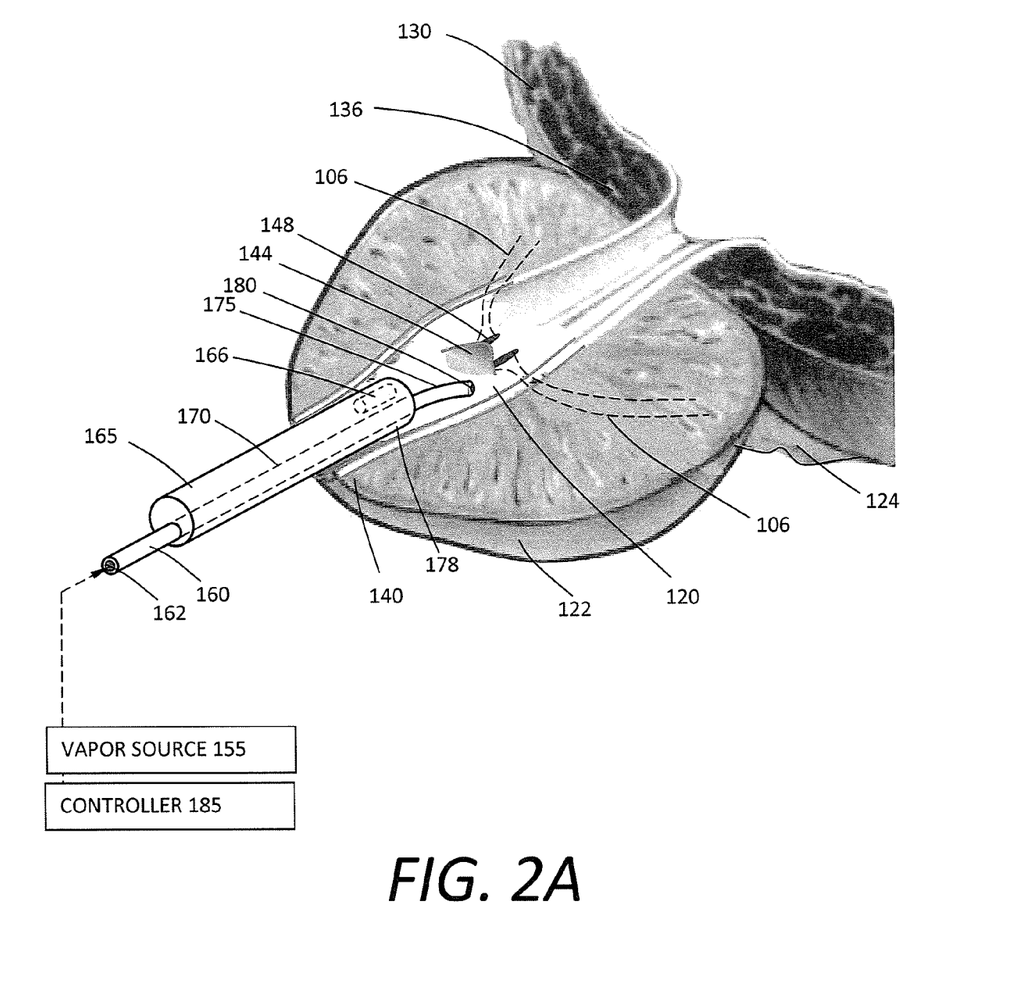
FIG. 2A is cut-away view of a patient's prostate and illustrating a method of introducing an endoscopic probe and vapor delivery tool according to the invention into a patient's prostatic urethra.

The two ejaculatory ducts, which carry sperm and the fluid secreted by the seminal vesicles 124, pass obliquely through the back portion of the prostate 122 and then narrow and converge toward the prostatic urethra 120 which is angulated at the verumontanum 144 (FIG. 2A). The ejaculatory ducts 106 empty into the urethra at the slit-like openings 148 (FIG. 2A). The prostatic urethra 120 then continues to the lower segment of the prostate 122 and exits near its apex 140. During ejaculation, semen passes through the ducts 106 and exits the body via the penis 150 (FIG. 1).

Figure 2B:
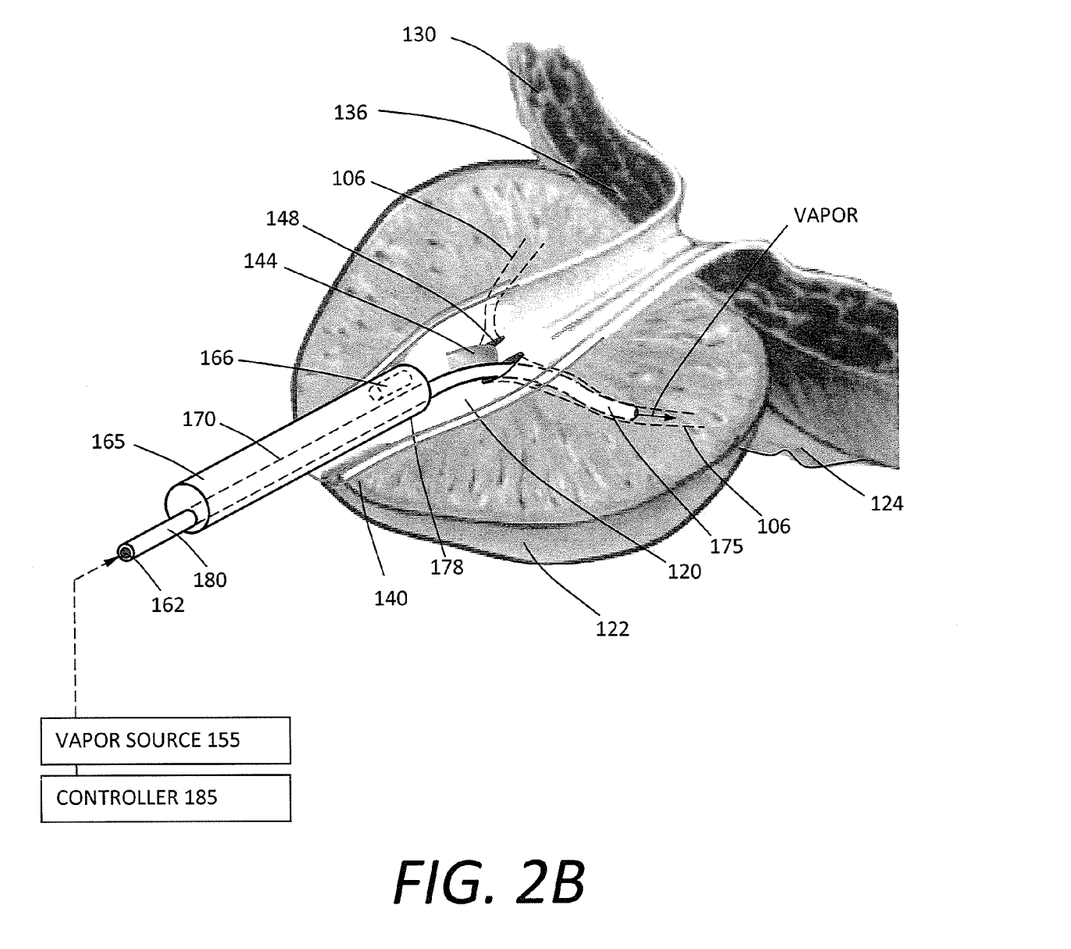
FIG. 2B is view of the patient's prostate as in FIG. 2A illustrating a subsequent step of inserting the vapor delivery tool into an ejaculatory duct and delivering a high-temperature condensable vapor therein.

Referring to FIGS. 2A and 2B, one method of the invention and related apparatus includes a system consisting of a vapor source 155 that is coupled to an elongated flexible vapor delivery probe or sleeve 160. The delivery probe or sleeve can be configured for introduction into a duct of the male reproductive system. In one embodiment, the vapor source 155 generates and delivers a heated vapor, for example water vapor, to a vapor-delivery lumen 162 in probe 160. Vapor generation systems are described in the following U.S. patent applications: Ser. No. 10/681,625, filed Oct. 7, 2003; Ser. No. 11/158,930, filed Jun. 22, 2005; Ser. No. 11/244,329, filed Oct. 5, 2005; Ser. No. 11/329,381, filed Jan. 10, 2006; Ser. No. 12/167,155, filed Jul. 2, 2008 and Ser. No. 12/389,808, filed Feb. 20, 2009. Further details of suitable vapor generation parameters and equipment may be found in US Pat. Pub. No. 2004/0068306.

Now turning to FIGS. 2A and 2B, an access device 165 such as a rigid or flexible endoscope can be navigated transurethrally to a region of the prostatic urethra 120 until anatomical landmarks are identified, such as the verumontanum 144 and/or the slit-like openings 148 of the ejaculatory ducts 106. The access tool can include a viewing device 166, such as the termination of fiber optic viewing means, a CCD or the like.

In FIGS. 2A-2B, the vapor delivery probe 160 can be advanced through a working channel 170 in access device 165 until a working end 175 of probe 160 exits the distal end 178 of the access device 165. The exiting of the delivery probe through the distal end can be observed by the viewing means 166. In one embodiment, referring to FIGS. 2A-2B, the working end 175 of vapor delivery probe 160 can have a memory curved configuration so that its extension from channel 170 can direct the end and vapor outlet 180 into the slit-opening 148 of an ejaculatory duct 106. In another embodiment, the working end 175 of vapor delivery probe 160 can include a pull wire for articulating the working end 175 for assisting in navigation.

FIG. 2B illustrates further advancement of working end 175 of probe 160 into the duct 106 a distance ranging from about 5 mm to 20 mm. The working end 175 can have suitable markings for viewing by the viewing means 166 to determine depth of penetration from the prostatic urethra into duct 106.

As can be understood from FIG. 2B, a next step of the method can include actuating the vapor source 155 and controller 185 to provide vapor (such as steam) into the probe. The steam can be produced in a handle portion of vapor delivery probe 160, or can be produced remotely by a vapor generator connected via a conduit coupled to the lumen 162 in the probe 160. The vapor can then be introduced into the ejaculatory duct 106 through outlet 180 in the distal end of the vapor delivery component or probe 160. In another aspect of the invention, vapor delivery and condensation of the vapor can apply energy to the duct sufficient to ablate, shrink and/or seal the duct. The method applies energy that denatures collagen in the lumen wall which can shrink and occlude the lumen of the duct 106. In one aspect of the invention, the vapor can have a temperature of at least 60° C., 70° C., 80° C., 90° C. or 100° C. The method further includes vapor delivery for an interval ranging from 0.1 second to 30 seconds, or alternatively, for an interval ranging from 1 second to 15 seconds.

In general, a method of the invention for vapor delivery to occlude a duct of the male reproductive system comprises introducing a vapor delivery tool or needle into a reproductive duct, and applying at least 1 W, 5 W, 10 W or 50 W of energy from the tool by means vapor energy release to ablate, shrink and/or occlude a duct. The method can cause localized ablation of the duct, and the applied energy from vapor can be localized without substantial damage to the prostate glandular tissue, the prostatic urethra 120 or nerves and other structures surrounding the prostate capsule.

Figure 3:
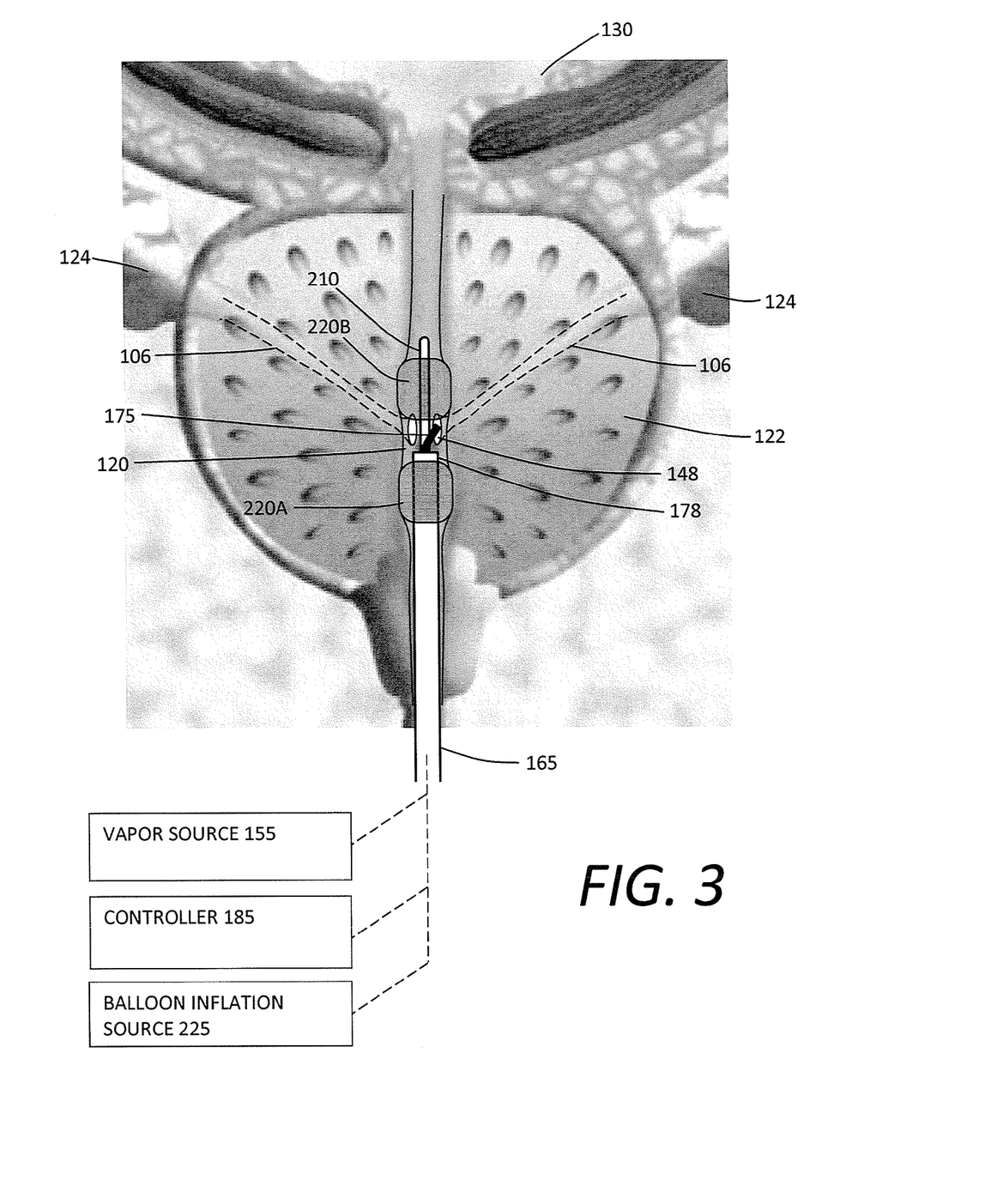
FIG. 3 is another schematic view of a patient's prostate illustrating a method of the invention wherein at least one expandable member is expanded in the prostatic urethra to retract, open and provide access to the ejaculatory ducts.

FIG. 3 shows another aspect of the invention wherein the method is similar to that of FIGS. 2A-2B, and includes providing the access tool 165 with an extendable member 210 that extends from the distal end 178 thereof. In the embodiment of FIG. 3, a seal can be formed or created in the urethra to contain the vapor within the urethra and to direct the vapor into the ejaculatory ducts. In one embodiment, the access tool 165 and the extendable member 210 each carry an inflatable balloon 220A and 220B, respectively, with a balloon inflation source 225 such as a syringe for inflating the balloons. The balloons can be sufficiently large for occlusion of the urethra (e.g., from about 2 mm to 10 mm in diameter) and can be spaced apart from about 5 mm to 25 mm or more. The balloons can be made of any material known in the art of catheter balloons, for example silicone or urethane. As can be understood from FIG. 3, the collapsed balloons can be maneuvered in collapsed configurations to either side of the openings 148 of ejaculatory ducts 106, and then expanded as a means of retracting the lumen of prostatic urethra 120 for the purpose of retracting and opening the slit-like open terminations of the ducts 106. In another optional step, $CO_2$ or another biocompatible gas can be introduced into the prostatic urethra 120 between the occlusion balloons 220A and 220B to expand and open the slit-like terminations 148 of ducts 106 to facilitate insertion of the vapor delivery probe. Thereafter, the distal end 175 of the vapor delivery probe 160 can be more easily advanced into each duct 106 sequentially for the delivery of vapor therein.

Figure 4:
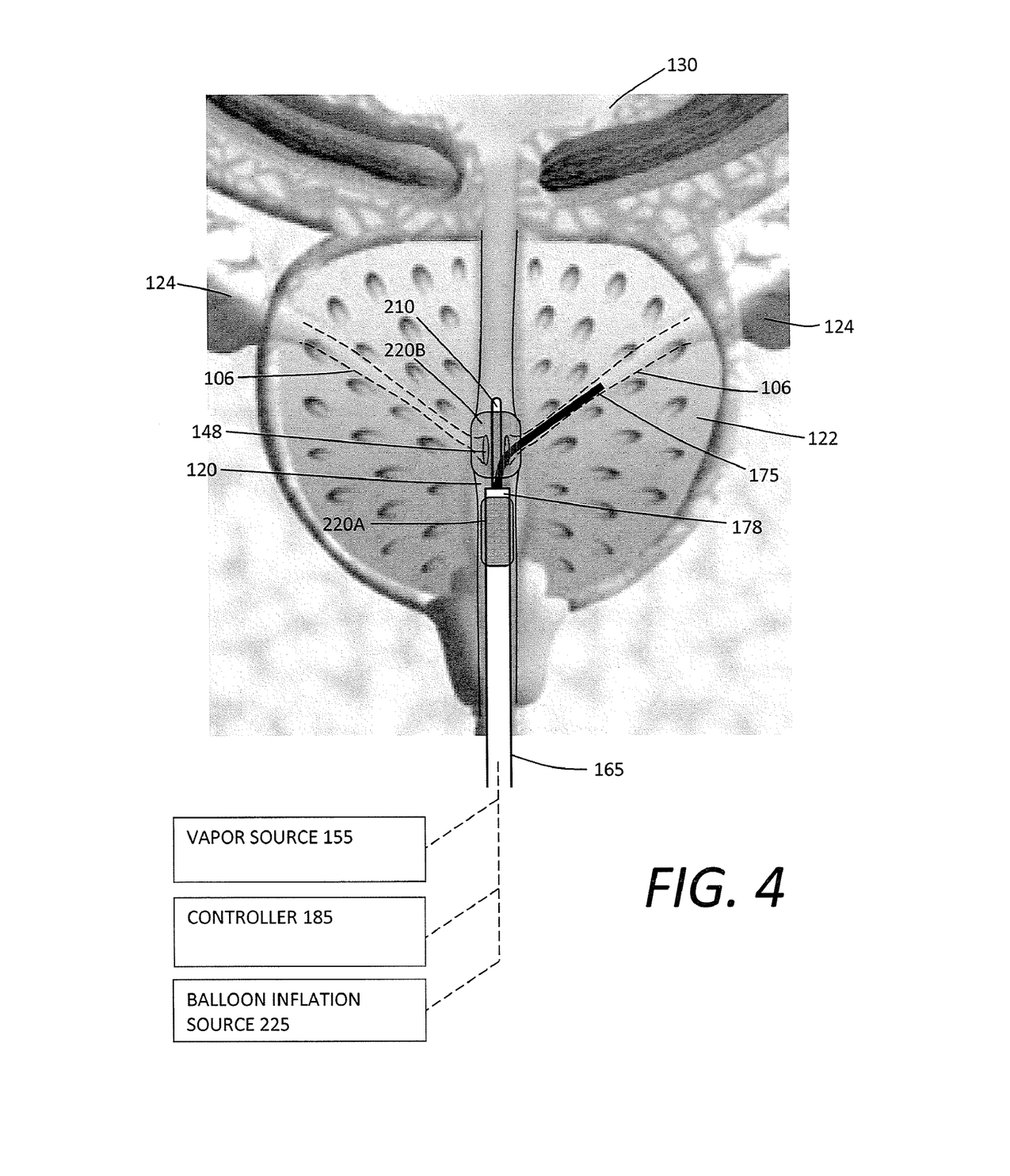
FIG. 4 illustrating another method of the invention which includes expanding and expandable member in the prostatic urethra against to open terminations of the ejaculatory ducts to seal the flow of vapor from a vapor delivery tool.

FIG. 4 shows another aspect of the invention the method which is similar to that of FIG. 3 with the additional step of re-positioning balloon 220B more proximally after the working end 175 of the vapor delivery tool 160 has been advanced into a duct 106. The expanded balloon as shown in FIG. 4 thus can seal the opening 148 of the duct and prevent back-flow of vapor into the prostatic urethra 120. In another embodiment and method, the extendable vapor delivery tool 160 can carry its own occlusion balloon (not shown) at its working end 175 to maintain the delivered vapor within the treated duct 106.

In another aspect of the invention, a method for male sterilization comprises introducing a thermal energy delivery member into duct of male reproductive system and applying energy from the member to ablate, seal and occlude the duct. Again, the energy delivery member can include means to deliver a heated vapor.

In another aspect of the invention, the method can include accessing a vas deferens through a skin incision and then penetration through the wall of the vas deferens.

In general, a method of occluding ejaculatory ducts comprises inserting a tool working end transurethrally to a region proximate a termination of a duct, the working end including a fluid-delivery channel, and delivering a flowable media through the channel into the duct to cause occlusion thereof. The method can include delivering a drug with the flowable media The method can further include delivering vapor through the channel and allowing the vapor to condense within the duct thereby applying heat to the duct. The method can include delivering a polymer or other occluding agent with the vapor. Stated alternatively, another method of the invention includes providing a vapor that carries a second composition, which can comprise a pharmacologic agent, a sealant, a glue or adhesive, a collagen composition, a polymer plug material, a fibrin or albumin or a particulate.

In another method and apparatus corresponding to the invention, the tool for accessing the urethra can include means for expanding and retracting the urethra with a non-condensable gas, such as $CO_2$, to allow simplified access for a tool into a duct 106. In one embodiment, the tool includes first and second axially spaced apart expandable members, such as occlusion balloons. The tool includes means to deliver a gas or a vapor from an outlet between the expandable members.

In one embodiment, the apparatus further includes a small diameter extendable member that can be directed and advanced into a lumen of a vas at least 1 mm, 5 mm, or 10 mm to deliver a treatment fluid, such as vapor, into the lumen of a duct.

Another method of the invention comprises introducing a device working end into a targeted site in the duct and actuating a heat emitter in the working end to occlude the lumen. The heat emitter can be at least one of an electrode, a light energy emitter, an ultrasound emitter, a resistive heating element, a microwave emitter, or an inductively heated emitter. The method can include transurethral introduction or can be inserted through a puncture or incision into the lumen of a reproductive duct.

Another method of the invention comprises introducing a device working end into a targeted region of an ejaculatory duct 106 or vas deferens and actuating a cooling or cryogenic means carried by the working end to modify the lumen. The method includes the cooling or cryogenic means injecting a flow media into the lumen in order to damage, occlude and seal the lumen.

In general, one system embodiment comprises a catheter or probe device configured for treating a reproductive duct that includes an elongated flexible member having an interior passageway extending to an outlet in a working end thereof, the member configured for transurethral introduction into the lumen of an ejaculatory duct, wherein the interior passageway in fluid communication with a vapor source capable of delivering a vapor media into the lumen of the duct to modify the duct. The device includes a vapor source that delivers a condensable vapor. The condensable vapor can have a temperature of at least 60° C., 70° C., 80° C., 90° C. or 100° C. The system further includes a controller for controlling a vapor delivery interval. In another embodiment, the system further includes an aspiration source for applying aspiration forces through the interior passageway of the catheter. The system optionally includes a source for introducing a second composition through the interior passageway. As described above, the source can carry a pharmacologic agent, a sealant, a glue or adhesive, a collagen composition, a polymer plug material, a fibrin or albumin or a particulate.

In another aspect of the invention, the introduction of the vapor probe and the delivery of vapor can be accomplished under any suitable type of imaging. In one method, the steps can be viewed by means of ultrasound or x-ray imaging. In one method, the probe introduction and energy delivery methods of the invention can be imaged by ultrasound means utilizing a trans-rectal ultrasound system commercialized by Envisioneering Medical Technologies, for example.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A male sterilization method comprising:
   introducing an endoscope through a patient's urethra to a prostate;
   introducing a vapor delivery tool through a channel in the endoscope;
   introducing the vapor delivery tool into or proximate to a duct of a male reproductive system;
   manipulating a curved distal end of the vapor delivery tool outwardly from the channel into or proximate to the duct of the male reproductive system; and
   delivering vapor media through the vapor delivery tool into the duct to occlude the duct.

2. The method of claim 1 further comprising forming a seal in the urethra to contain the vapor media.

3. The method of claim 2 wherein the seal directs the vapor media into the duct.

4. The method of claim 2 wherein the step of forming the seal includes expanding an expandable member.

5. The method of claim 2 wherein the step of forming the seal includes expanding an expandable portion of the vapor delivery tool.

6. The method of claim 1 wherein the vapor media carries a second composition.

7. The method of claim 6 wherein the second composition comprises a pharmacologic agent.

8. The method of claim 6 wherein the second composition comprises a sealant.

9. The method of claim 1 wherein the introducing step comprises introducing the vapor delivery tool transurethrally.

10. The method of claim 1 wherein the introducing step comprises introducing the vapor delivery tool through a skin incision.

11. The method of claim 1 wherein the vapor media damages a wall of the duct.

12. The method of claim 1 wherein the vapor media denatures collagen in the wall of the duct.

13. The method of claim 1 wherein the vapor media has a temperature of at least 60° C.

14. The method of claim 1 wherein the vapor media has a temperature between approximately 60° C. and 100° C.

15. The method of claim 1 wherein the vapor media is delivered for an interval ranging from approximately 0.1 second to 30 seconds.

16. The method of claim 1 wherein the duct is an ejaculatory duct.

17. The method of claim 1 wherein the duct is a ductus deferens.

18. The method of claim 1 wherein the manipulating step comprises advancing a shape memory distal end outwardly from the channel to provide the curved distal end.

19. The method of claim 1 wherein the manipulating step comprises actuating a pull-wire to provide the curved distal end.

20. A system for male sterilization comprising:
   a vapor delivery probe configured for transurethral introduction through a working channel of an endoscope into or proximate to a duct of a male reproductive system, the vapor delivery probe including a distal end comprising a shape memory material configured to provide a memory curved shape when advanced outwardly from the working channel; and
   a vapor media source in fluid communication with the vapor delivery probe, the vapor media source adapted to deliver a vapor media through the vapor delivery probe into the duct.

21. The system of claim 20 further comprising at least one expandable member configured to contain the vapor media.

22. The system of claim 21 wherein the at least one expandable member is an inflatable balloon.

23. The system of claim 20 wherein condensable vapor has a temperature of approximately 60° to 100° C.

24. The system of claim 20 further comprising a source for introducing a second composition through the vapor delivery probe.

25. The system of claim 20 further comprising a controller configured to control a vapor delivery interval.

26. A male sterilization method comprising:
   introducing an endoscope through a patient's urethra to a prostate;
   inserting a vapor delivery tool through a channel in the endoscope into or proximate to a duct of a male reproductive system;
   expanding an expandable member carried by the vapor delivery tool in the urethra such that the expandable member spans a termination of the duct; and
   delivering a vapor media from the vapor delivery tool to occlude the duct.

27. The method of claim 26 wherein the vapor media is selected from the group consisting of a cryogenic fluid, a heated liquid, and high temperature vapor.

* * * * *